(12) United States Patent
Haritou et al.

(10) Patent No.: US 11,919,281 B2
(45) Date of Patent: Mar. 5, 2024

(54) DOUBLE SKIN STRUCTURE WITH INTERSTITIAL SPACER

(71) Applicants: Christos Sotirious Haritou, New Marske (GB); Alan Fada, Washington (GB)

(72) Inventors: Christos Sotirious Haritou, New Marske (GB); Alan Fada, Washington (GB)

( * ) Notice: Subject to any disclaimer, the term of this patent is extended or adjusted under 35 U.S.C. 154(b) by 316 days.

(21) Appl. No.: 17/273,817

(22) PCT Filed: Sep. 5, 2019

(86) PCT No.: PCT/GB2019/052471
§ 371 (c)(1),
(2) Date: Mar. 5, 2021

(87) PCT Pub. No.: WO2020/049302
PCT Pub. Date: Mar. 12, 2020

(65) Prior Publication Data
US 2021/0339497 A1  Nov. 4, 2021

(30) Foreign Application Priority Data

Sep. 5, 2018 (GB) ...................... 1814458

(51) Int. Cl.
*B32B 3/02* (2006.01)
*B32B 5/02* (2006.01)
(Continued)

(52) U.S. Cl.
CPC ............... *B32B 3/02* (2013.01); *B32B 5/022* (2013.01); *B32B 5/263* (2021.05); *B32B 7/08* (2013.01);
(Continued)

(58) Field of Classification Search
CPC ........... B32B 3/02; B32B 5/022; B32B 5/263; B32B 7/08; B32B 7/12; B32B 2255/02;
(Continued)

(56) References Cited

U.S. PATENT DOCUMENTS 4,537,329 A * 8/1985 Norton ................. B65D 90/044
                                                                220/661
4,818,976 A * 4/1989 Schmitt ................. G01F 23/245
                                                                340/622

(Continued)

*Primary Examiner* — Matthew D Matzek
(74) *Attorney, Agent, or Firm* — Kinney & Lange, P.A.

(57) ABSTRACT

A fluid impervious wall skin provides an interstitial space. The wall is formed from a composite material, the composite material comprising a plurality of layers including:, a first layer of flexible material having adhesive on at least one surface thereof for attachment to a structural wall; a layer comprising a spacer; and a second layer of flexible material; the layers of the composite material are attached a structural wall and one to the other by adhesive between adjacent layers, and the spacer provides the interstitial space N between the said first and second layers of flexible material within the said composite material. The second flexible layer comprises heavier than the second weight, wherein the each overlapping sheet presents a free edge, and the tape is positioned over the free edge is attached to the overlapping and the overlapped sheet of woven fibreglass fabric of the first weight, and a solvent free epoxy coating applied to the surface of the second flexible layer that is distal from the structural wall, which coating cures to form a hard fluid impervious layer.

22 Claims, 13 Drawing Sheets

(51) Int. Cl.
  *B32B 5/26* (2006.01)
  *B32B 7/08* (2019.01)
  *B32B 7/12* (2006.01)
  *B65D 90/02* (2019.01)
  *B65D 90/51* (2019.01)
  *G01D 11/24* (2006.01)

(52) U.S. Cl.
  CPC ............... *B32B 7/12* (2013.01); *B65D 90/02* (2013.01); *B65D 90/51* (2019.02); *G01D 11/245* (2013.01); *B32B 2255/02* (2013.01); *B32B 2255/26* (2013.01); *B32B 2262/101* (2013.01); *B32B 2307/536* (2013.01); *B32B 2307/718* (2013.01); *B32B 2307/7265* (2013.01); *B32B 2307/732* (2013.01); *B32B 2405/00* (2013.01); *B32B 2439/00* (2013.01); *B65D 2590/023* (2013.01)

(58) Field of Classification Search
  CPC .......... B32B 2255/26; B32B 2262/101; B32B 2307/536; B32B 2307/718; B32B 2307/7265; B32B 2307/732; B32B 2405/00; B32B 2439/00; B32B 2262/02; B32B 2307/714; B32B 2439/40; B32B 2571/00; B32B 2597/00; B32B 2607/02; B32B 3/06; B32B 3/08; B32B 5/06; B32B 5/26; B32B 15/14; B32B 17/02; B32B 29/02; B32B 3/04; G01D 11/245; G01N 17/006; G01N 33/208; G01N 2033/0096; B65D 90/028; B65D 90/501; B65D 90/022; B65D 2590/023; B65D 90/05; B65D 90/02
  USPC .............................................. 428/343, 299.4
  See application file for complete search history.

(56) References Cited

U.S. PATENT DOCUMENTS

| | | | |
|---|---|---|---|
| 4,849,150 A * | 7/1989 | Kittaka | B29D 23/001 264/258 |
| 2007/0104958 A1 * | 5/2007 | Golden | B32B 7/12 521/76 |
| 2010/0075086 A1 * | 3/2010 | Haritou | B32B 5/022 442/41 |
| 2017/0021587 A1 * | 1/2017 | Haritou | B32B 5/028 |
| 2017/0369238 A1 * | 12/2017 | Goad | B29C 65/54 |

* cited by examiner

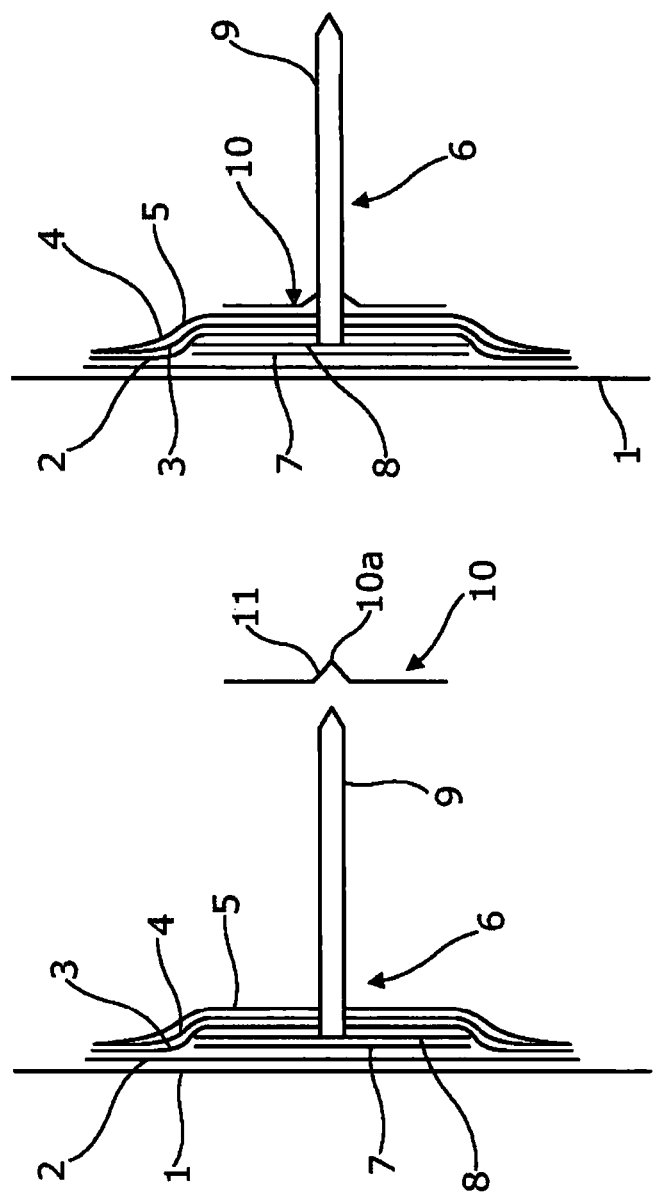

DOUBLE SKIN STRUCTURE WITH INTERSTITIAL SPACER

FIELD OF THE INVENTION

The present invention relates to double skinned structures. Typically one skin of such structures is provided by a wall, such as a tank wall, with the second skin attached to the wall. The interstitial space provided between the two skins is monitorable, for example by exerting a vacuum on the interstitial space between a two skins.

BACKGROUND OF THE INVENTION

Structures, such as tanks are commonly used for storing fluids. Environmental damage may occur if a fluid storage tank leaks. Obviously the nature and extent of damage caused by leakage from a tank will depend on the nature of the fluid in the tank and the amount of leakage. Where tanks are above-ground, they can be monitored by visual inspection. Nevertheless, the ability to monitor the integrity of an above-ground tank would save labour and provide for monitoring of those parts of the tank that are difficult to inspect. In many circumstances fluid storage tanks are located underground. Underground fuel storage tanks are used at filling stations for the storage of petroleum products. Leakage of petroleum products from an underground storage tank might go unnoticed for many months, during which time water courses may be polluted, and soil may be contaminated. Furthermore, people and buildings in the vicinity may be endangered by the presence of highly flammable fuels in the ground.

Historically, underground fuel storage tanks were fashioned from a single skin of mild steel. Corrosion of such tanks was not a problem whilst petrol fuel contained lead, the lead acting as a corrosion inhibitor. However, in most countries lead is no longer present in petrol fuel. The resulting petrol fuel is corrosive of steel, and there have been a number of incidences of such tanks leaking fuel into the ground with consequent damaging effects. There is therefore a move to line underground fuel storage tanks with linings not susceptible to corrosion by the fuel destined to be stored in the tank.

If a double skinned tank contains an air gap between the outer tank wall and the interior lining, leakage from the tank can be monitored by various leak monitoring devices. One such leak monitoring device monitors a vacuum in the air gap. A change in pressure indicates an integrity failure in the inner lining or outer hull.

The replacement of an underground tank is a time consuming and expensive process, since in the case of a filling station, the cost of physically removing the tank from the ground is itself high, but more importantly whilst the tank is being replaced the fuel station must be closed, resulting in loss of revenue for the period of closure, and possible long-term loss of business due to customers going to other filling stations during the period of closure.

Re-lining existing underground tanks provides at least three benefits. First, the lining is typically selected so as not to be corrodible by the fuel. Second, if there is an interstitial space this space can be monitored to establish whether there is any leakage of fuel from the tank, and third, lining a tank can be accomplished more quickly than replacement of a tank.

The publication WO 00/32394 describes a method of lining a fuel storage tank in which a keying means is applied to the surface of a tank. A corrosion barrier is then applied to the keying means. An interstitial grid is then applied to the tank and pliable glass reinforced plastics material is laid onto the grid. The glass reinforced plastics material is then exposed to ultra violet rays to cure the material and form a hardened inner liner shell for the tank.

To line a tank following the method described in WO 00/32394 requires a team of men working for thirty to forty five days, with one man of the team working in the tank at any one time. Due to the toxic nature of the gases given off by the resins used in the laying up of the pliable glass reinforced plastics material onto the grid, and the ability of those gases to pass through the skin and into the bloodstream of humans, the length of time a worker may spend in the tank is severely limited, and special protective clothing must be worn and breathing apparatus used. Whilst in the tank the workers wear clothing that is impervious to the gases given off by the resins used in the laying up of the glass reinforced plastics material. However, the protective clothing available is only impervious to these gases for a limited period of time, after which the worker must come out of the tank, dispose of the protective clothing and be de-contaminated. The risk of hospitalisation resulting from exposure to noxious gases during the laying up the glass reinforced plastics material is significant.

Another apparatus and method of lining a tank is disclosed in GB 2413587. This apparatus requires the tank to be lined with a material having protrusions on one side, the free ends of which face the inner wall of the tank and are glued thereto. Seams between adjoining sections of material may be joined together, or a second layer of material may cover the first, with adjoining sections thereof being attached to each other to form a sealed lining. Whilst this re-lining apparatus and method provides for effective sealing and reduces the problems associated with working in a confined environment when exposed to noxious gases, performance of the method of re-lining is time consuming.

Another apparatus and method of lining a tank is disclosed in PCT/GB2006/050069. In this apparatus and method the tank is lined with a single layer of fluid impervious plastics material. An interstitial space exists between opposing faces of said wall and said plastics sheet which is monitored by a vacuum. This apparatus and method uses fewer and less costly materials than the method of GB 2413587, and the time required to perform the method is reduced. Nevertheless an apparatus and method yet more efficient would be desirable.

An apparatus and method for lining a tank so as to provide a monitor able interstitial space is described in GB2444486. The apparatus uses sheet material having adhesive applied to both sides to attach itself and other components of the lining to the wall of the tank. The apparatus and method described in this invention have been found to be particularly effective in the lining of both underground and above-ground fuel storage tanks.

The apparatus of one embodiment of GB244486 includes a layer of fibreglass. It has been found that where edges of sheets of fibreglass abut one another the free ends of individual fibres may be difficult to encapsulate with resin.

It has also been found that where the tank to be lined is severely corroded the adhesive may not succeed in adhering the sheet to the surface of the tank.

Further, there is a constant desired to reduce application times.

It has also been recognised that above-ground tanks are susceptible to corrosion, in particular external corrosion, especially in the bottom walls thereof.

It would therefore be desirable to provide an improved apparatus and method.

SUMMARY OF THE INVENTION

According to a first aspect of the invention there is provided a fluid impervious wall skin providing an interstitial space, the wall formed from a composite material, the composite material comprising a plurality of layers including:
  i. a first layer of flexible material having adhesive on at least one surface thereof for attachment to a structural wall;
  ii. a layer comprising a spacer; and
  iii. a second layer of flexible material;
wherein layers of the composite material are attached a structural wall and one to the other by adhesive between adjacent layers, and wherein the spacer provides the interstitial space between the said first and second layers of flexible material within the said composite material and a solvent free epoxy coating applied to the surface of the second flexible layer that is distal from the structural wall, which coating cures to form a hard fluid impervious layer.

Advantageously, the second flexible layer comprises overlapping sheets of a woven fibreglass fabric of a first weight and a woven fibreglass fabric tape of a second weight, the first weight heavier than the second weight, wherein the each overlapping sheet presents a free edge, and the tape is positioned over the free edge is attached to the overlapping and the overlapped sheet of woven fibreglass fabric of the first weight.

Typically, the resulting hard fluid impervious layer has a Shore D hardness reading of between 75 and 90, more preferably between 80 and 90, still more preferably between 85 and 88, and most preferably in the range of 85.5 to 87.5.

The fluid impervious wall skin may further comprise a third layer of flexible material, wherein the third layer is itself fluid impervious and wherein the third layer is situated between the spacer and the second layer of flexible material.

Advantageously, the first layer of flexible material is coated with adhesive on both sides thereof.

Preferably, the first layer of flexible material is selected from the group comprising: paper, paper coated with adhesive, paper impregnated with adhesive, plastics film, and plastics film coated with adhesive.

It is preferred that the third layer is selected from the group comprising: a metallic foil, a vinyl film and a pvc film.

Preferably, the second layer is coated with adhesive on one side thereof.

Preferably, the third layer is coated with adhesive on one side thereof.

The fluid impervious wall skin may include a peel off layer for each adhesive coated surface.

Advantageously, the spacer is a permeable membrane.

The permeable membrane may be a thermoplastic and may be a non-woven grid.

It is preferred that the woven fibreglass fabric of a first weight weighs between 150 g/m2 and 250 g/m2 and a woven fibreglass fabric tape of a second weight weighs between 50 and 150 g/m2.

More preferably the woven fibreglass fabric of a first weight weighs between 175 g/m2 and 225 g/m2 and a woven fibreglass fabric tape of a second weight weighs between 75 and 125 g/m2.

Still more preferably, the woven fibreglass fabric of a first weight weighs between 190 g/m2 and 210 g/m2 and a woven fibreglass fabric tape of a second weight weighs between 90 and 110 g/m2.

Most preferably, the woven fibreglass fabric of a first weight weighs 200 g/m2 and a woven fibreglass fabric tape of a second weight weighs 106 g/m2.

It is preferred that the solvent free epoxy coating has a nominal thickness of at least 1000 micron.

Preferably, the solvent free epoxy coating has a nominal thickness of at least 1270 micron More preferably, wherein the solvent free epoxy coating has a nominal thickness of at least 2000 micron.

Advantageously, in and around woven fibreglass fabric tape the solvent free epoxy coating has a nominal thickness that is double the nominal thickness of the solvent free epoxy coating between adjacent tape covered overlapped edges.

The fluid impervious wall skin may further comprise at least one anchor, the or each anchor spaced apart relative to other anchors of the plurality of anchors.

It is preferred that the plurality of anchors are situated in an upper region of the structure.

The or each anchor may comprise an additional adhesive between the first layer and the structural wall.

The or each anchor comprises a pin and clasp, the pin projecting through the layers of flexible material, and the clasp mounted on the pin and pressing against the surface of the second layer of flexible material distal from the structural wall, and wherein the clasp and the end of the pin are encapsulated by the solvent free epoxy coating.

Advantageously, the wall skin includes a coating of solvent free epoxy coating applied to the inner surface of the structural wall, the first layer attached to the cured structural wall coating.

Preferably, the structural wall coating has a nominal thickness of at least 500 micron.

The fluid impervious wall skin may further comprise at least one housing attached to the structural wall and extending to the same side thereof as the wall skin, the housing having a removable and closure member that is fluid tight when closed, wherein at least the closure member of the or each at least one housing is not covered by the fluid impervious wall skin, the housing providing access to a part of the structural wall.

The at least one housing may include a plate for attachment to the structural wall and a chamber that is attached to the plate, the closure member located in an opening in the chamber.

The plate may have an opening therein through which access to the structural wall may be gained, and wherein the chamber has a corresponding opening, the two openings being aligned when the chamber is mounted on the plate.

The fluid impervious wall skin may further comprise monitoring means configured for monitoring the condition of the structural wall.

The monitoring means may comprise at least one sensor.

The at least one sensor may be connected to an external data receiving by a wired or wireless connection.

The at least one sensor may be situated between the structural wall and the first layer of flexible material of the wall skin.

The monitoring means may be mounted in the housing or within a protective member.

According to a second aspect of the invention there is provided a method of fabricating a fluid impervious wall skin as claimed in any preceding claim, comprising the steps of:
  i. cleaning an inner surface of a structural wall;
  ii. attaching the first layer of flexible material to the coated inner surface of the structural wall;

iii. building up subsequent layers of sheet material of the composite material on to the first layer one on top of the other;

iv. attaching the woven fabric tape of the second flexible layer to the overlapping sheets of a woven fibreglass fabric of said second flexible layer so as to cover the free overlapping edge of the overlapping sheets;

v. applying the solvent free epoxy coating to the surface of the second flexible layer that is distal from the structural wall, which coating cures to form a hard fluid impervious layer; and vi. curing the said coating.

It is preferred that the method includes the additional step of applying a structural wall coating of solvent free epoxy resin to the cleaned inner surface of the structural wall. The structural wall coating may have nominal thickness of at least 500 micron.

Preferably, the method includes the step of making a vacuum connection through the surface to be lined to the interstitial space.

The method may comprise the step of applying a vacuum to the interstitial space prior to the application of the curable material.

The method of fabricating a fluid impervious wall skin may comprise the step of providing at least one anchor adapted to anchor the fluid impervious wall skin to the structural wall, wherein the or each anchor is provided by:

cutting a flap in the layers of sheet material between steps iv and v to reveal the coating applied to inner surface of the structural wall in step i;

abrading the coating;

applying an adhesive that is compatible with the abraded coating and pressing the flap of layers on to the adhesive.

The method of fabricating a fluid impervious wall skin may comprise the step of providing at least one anchor adapted to anchor the fluid impervious wall skin to the structural wall, wherein the or each anchor is provided by:

attaching a support element including a piercing member to the structural wall of after step i;

between steps iv and v sliding the clasp on to and along the piercing member of the anchor so that the face of the clasp proximate the wall presses onto the layer of the composite material most proximate the clasp;

removing the portion of the piercing member extending beyond the face of the clasp distal from the wall.

The method may include the step of attaching at least one housing to the structural wall, the housing extending to the same side thereof as the wall skin, the housing having a removable and closure member that is fluid tight when closed, wherein at least the closure member of the or each at least one housing is not covered by the fluid impervious wall skin, the housing providing access to a part of the structural wall.

The method may include the step of providing a monitoring means configured for monitoring the condition of the structural wall. The monitoring means may comprise at least one sensor.

The method may include the step of arranging the at least one sensor between the structural wall and the first layer of flexible material of the wall skin.

According to a third aspect of the invention there is provided a structural wall having attached thereto a fluid impervious wall skin providing an interstitial space, the wall formed from a composite material, the composite material comprising a plurality of layers including:

i. a first layer of flexible material having adhesive on at least one surface thereof for attachment to a structural wall;

ii. a layer comprising a spacer; and iii. a second layer of flexible material;

wherein layers of the composite material are attached a structural wall and one to the other by adhesive between adjacent layers, and wherein the spacer provides the interstitial space between the said first and second layers of flexible material within the said composite material and a solvent free epoxy coating applied to the surface of the second flexible layer that is distal from the structural wall, which coating cures to form a hard fluid impervious layer.

At least one housing may be attached to the structural wall and extending to the same side thereof as the wall skin, the housing having a removable and closure member that is fluid tight when closed, wherein at least the closure member of the or each at least one housing is not covered by the fluid impervious wall skin, the housing providing access to a part of the structural wall.

The at least one housing may include a plate for attachment to the structural wall and a chamber that is attached to the plate, the closure member located in an opening in the chamber.

The plate may have an opening therein through which access to the structural wall may be gained, and wherein the chamber has a corresponding opening, the two openings being aligned when the chamber is mounted on the plate.

The fluid impervious wall skin may further comprise monitoring means configured for monitoring the condition of the structural wall.

The monitoring means may comprise at least one sensor.

The at least one sensor may be connected to an external data receiving by a wired or wireless connection.

The at least one sensor may be situated between the structural wall and the first layer of flexible material of the wall skin.

The monitoring means may be mounted in the housing or within a protective member, for example a cap. The protective member may be attached to the structural wall by an adhesive. Advantageously, protective member is devoid of sharp edges.

The protective member may be shaped and dimension relative to the monitoring means such that a space exists between the cap and the monitoring means.

The sensor may be attached to the structural wall by a suitable adhesive.

BRIEF DESCRIPTION OF THE DRAWINGS

In the drawings, which illustrate preferred embodiments of the invention, and which are by way of example:

FIG. 7 is a cross-sectional elevation of the wall skin illustrated in FIG. 6 in one stage of construction;

FIG. 8 is a cross-section of the wall skin illustrated in FIGS. 6 an 7 in a second stage of construction;

FIG. 11b is an exploded view of assembled components illustrated in FIG. 11a;

DETAILED DESCRIPTION OF THE PREFERRED EMBODIMENTS

Figure 1:
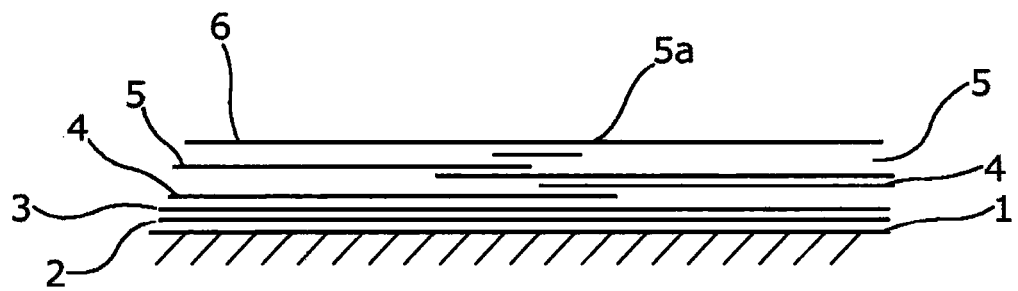
FIG. 1 is schematic cross-sectional representation showing the different layers of the fluid impervious wall skin of the invention.

Referring now to FIG. 1, which illustrates a wall 1 typically forming part of a tank or other substantially hollow structure and a lining for the wall. In most circumstances the lining will be on the inside of the wall 1. However, this does not preclude the lining being on the outside of the wall.

In most circumstances where the double skin structure of the invention is to be formed the wall 1 of the existing structure, the tank wall for example, is corroded. The first layer 2 needs a smooth surface to adhere to. The surface of wall 1 is prepared by cleaning, typically by shot blasting and then a layer of solvent free resin is applied to a thickness of between 500 micron and 1500 micron. Where there has been significant surface corrosion the surface can be pitted post cleaning. Where such surface pitting exists the nominal thickness of the solvent free resin coating will typical be 1270 micron or greater and preferably in the range 1270-1500 micron. Where there is little or no pitting the solvent free resin coating is applied to a nominal thickness of 500 micron to 1000 micron. Nominal thickness means an average of the thicknesses of the coating measured at a number of, for example 100, points. The solvent free resin is usually applied by spraying using equipment that is widely available and known in the art. In the illustrated example, the solvent free resin is a two component polycyclamine epoxy and includes glass flake and fibre reinforcement. The polycyclamie epoxy is a novolac epoxy resin. One solvent free resin having these properties is Enviroline (registered trade mark) 376F-60 (SPL) available from Akzo Nobel.

The solvent free resin coat is allowed to cure for 24 hours. The surface provided by the cured resin is in itself impervious to fluids such as water, fuel, oil etc. If the solvent free coating is applied to a sufficient thickness, that is greater than 1270 micron, the cured solvent free epoxy resin coating can bridge holes in the metal of wall 1 of up to 50 mm diameter.

If after cleaning, pits in the wall are too deep to be covered adequately by the sprayed on solvent free epoxy resin, any such pits can be filled with a two part epoxy filler that is compatible with the solvent free epoxy resin. Once pits are filled the solvent free epoxy coating may be applied to the cleaned metal surface and any filler applied thereto. Suitable fillers include Hempel ProFiller 35370 from Hempel A/S and AWLFAIR LW D8200/D7200 from Akzo Nobel.

A first layer of flexible material 2 has adhesive to both sides thereof. The flexible material may be a paper that is impregnated with adhesive. Alternatively, a flexible material may be coated with adhesive on both sides thereof. In order that the flexible material 2 may be transported and handled easily it is preferred that each surface thereof is provided with a peel-off material, which reveals the sticky surface when peeled off. The peel-off layer is removed from one surface of the flexible material 2 and that surface is presented up to and pressed on to the adjacent surface of the wall 1. With the peel-off material removed from the other surface of the flexible material 2 of the first later, a layer of non-woven grid material 3 is attached to the surface of the flexible material 2 that is distal from the wall 1. The non-woven grid material 3 is open and highly permeable. In the present example the non-woven grid material 3 is a thermoplastic and comprises a first set of spaced apart strands 3' oriented in one direction and a second set of spaced apart strands 3" oriented in another direction, for example the strands 3" may lie at an angle of 60 degrees to the strands 3'. The second set of strands 3" lie on top of and are fixed to the first set of strands 3'. In the illustrated embodiment the strands are approximately 0.5 mm in cross-section, spaced apart at centre to centre intervals of 3 mm. The overall thickness of the non-woven grid material is approximately 1 mm.

A woven mesh could also be used to provide the interstitial space.

Figure 2:
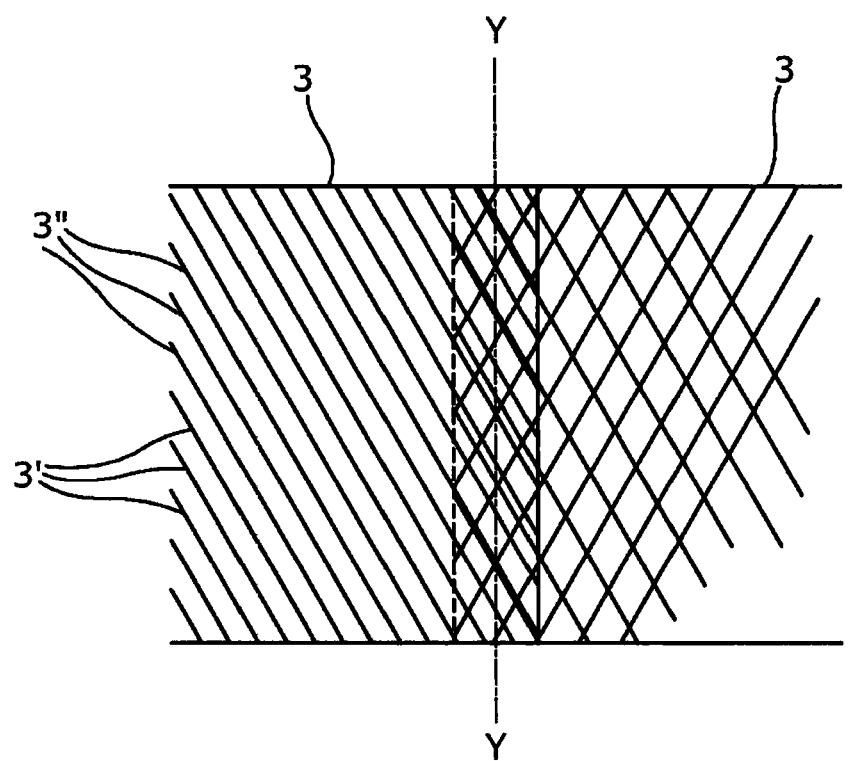
FIG. 2 is a schematic representation of a spacer layer of the wall skin illustrated FIG. 1.

In most circumstances individual pieces of the non-woven grid material are smaller than the area of wall to be covered. The preferred method of forming a joint between adjacent pieces of non-woven grid material is to overlap the edge of one piece over the edge of an adjacent piece, then to cut along the centre line Y-Y of the overlap to form a precise butt joint as shown in FIG. 2.

A third flexible layer 4 is fluid impervious and in the illustrated example is a foil sheet, preferably a metal foil. The foil sheet has adhesive applied to one side thereof and for convenience of transportation and application is provided with a peel-off layer (not shown) which is removed prior to application of the foil sheet to the non-woven grid material 3.

Figure 3:
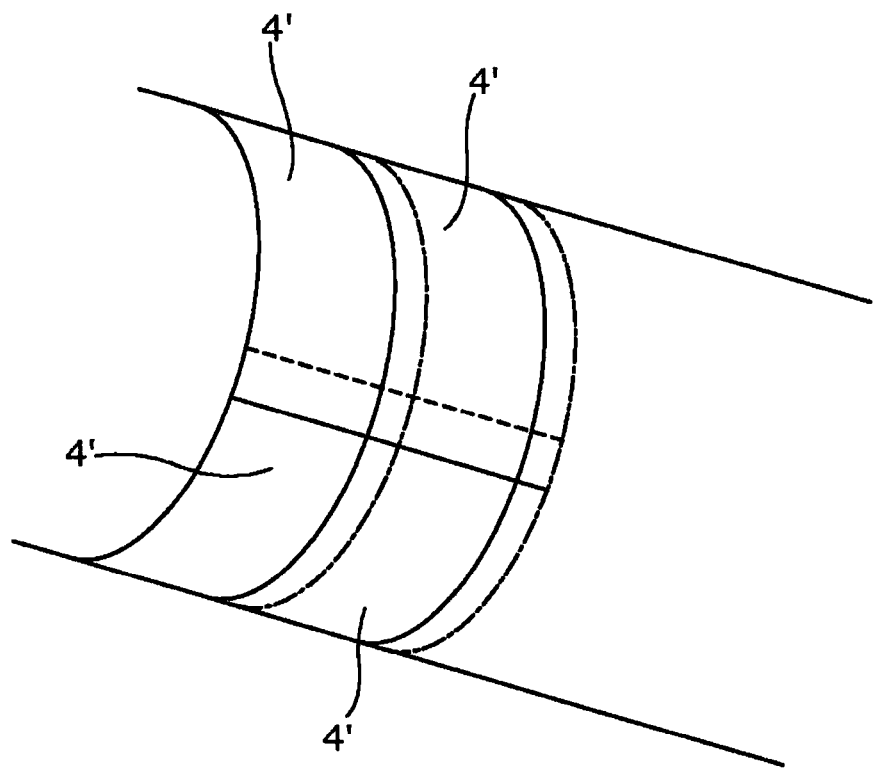
FIG. 3 is a schematic representation of a fluid impervious layer of the wall skin illustrated in FIG. 1.

It is also necessary in most circumstances to use more than one piece of foil. Hence the third layer 4 typically includes overlapped joints, as shown in FIG. 3. In the illustrated example individual pieces of foil are 500 mm wide and have a thickness of 50 micron. Where two sheets overlap, the overlap distance is typically between 50 and 100 mm. A greater overlap distance is possible but of course uses additional material.

The fourth layer of material comprises woven sheets of a fibreglass cloth 5 in combination with a woven fibreglass cloth in the form of a tape 5a. The fibreglass cloth 5 has a weight of 200 g/m2 (with a tolerance of +/−10%), a nominal thickness of 0.24 mm a thread count of 8/cm in the warp and 6.5/cm in the weft.

The sheets of fibreglass cloth are 500 mm wide and are laid with an overlap of between 50 and 100 mm. The free edge of the overlapping sheets present individual strands. These can cause problems when the final resin coating is applied. This problem has been overcome by applying a tape 5a of a very similar material over the free edge of the overlapping sheets. The tape 5a is lighter than the fabric of the sheets. The tape has a nominal thickness of 0.13 mm and a weight of 106 g/m2. The thread count is 24/cm in the warp and 623/cm in the weft. The tape is 50 mm wide, although tapes that are both narrower and wider may be contemplated.

The minimum width is determined by the requirement to overlie the free edge of the overlapping sheets woven fibreglass cloth 5.

Both the sheets of woven fibreglass cloth 5 and the tape 5a are provided with an adhesive applied to one side thereof and for convenience of transportation and application a peel-off layer (not shown) is provided to cover the adhesive. The peel-off layer is removed prior to application of the foil sheet to the non-woven grid material 3.

Following installation of the fibreglass cloth layer comprised of the sheet 5 and tape 5a, a solvent free epoxy resin is applied across the whole surface of the fibreglass to a thickness of 2000 micron. In the regions of the tape 5a, it is preferred to apply a 'stripe' coat over and immediately adjacent the tape 5a prior to application of the coat covering the whole surface of the fibreglass cloth layer. Typically, the stripe coat also has a nominal thickness of 2000 micron. Hence, where a stripe coat is used, some areas of the tank will have a nominal coating thickness of 4000 micron. Typically the solvent free epoxy resin is applied to structures section by section. When application moves from a finished section to the next section, the solvent free coating applied to the next section is overlapped on to the previously finished section and hence in the region of overlap the coating is double the thickness of areas where there is no overlap.

Also, it is typically the case that the solvent free epoxy coating is applied in two passes. It is preferred that the second pass is substantially perpendicular to the first pass, although this is not essential. The coating applied by two passes is considered as a single coat as the solvent free epoxy coating applied in the second pass is applied while the solvent free epoxy from the first pass is wet, i.e. the first pass is not allowed to cure before the second pass is applied. It is preferred that substantially equal amounts of solvent free epoxy are applied in the first and second passes.

The epoxy resin is applied using a spray gun in which the resin is heated to a maximum of 60° C. in the spray applicator. In the illustrated example the epoxy resin is a two component polycyclamine epoxy and includes glass flake and fibre reinforcement.

It has been found that by adopting a relatively heavy woven fibreglass cloth, epoxy resin may be applied thereto in a single layer that is thicker than where a lighter weight of woven fibreglass cloth is used. Furthermore, the epoxy resin can be applied in a single coat, or a single full coat with a stripe coat covering any areas of tape 5a as described above.

The advantage of applying the epoxy resin in a single relatively thick coat is that fewer pinhole result in the cured resin when compare to two thinner coats.

Figure 4:
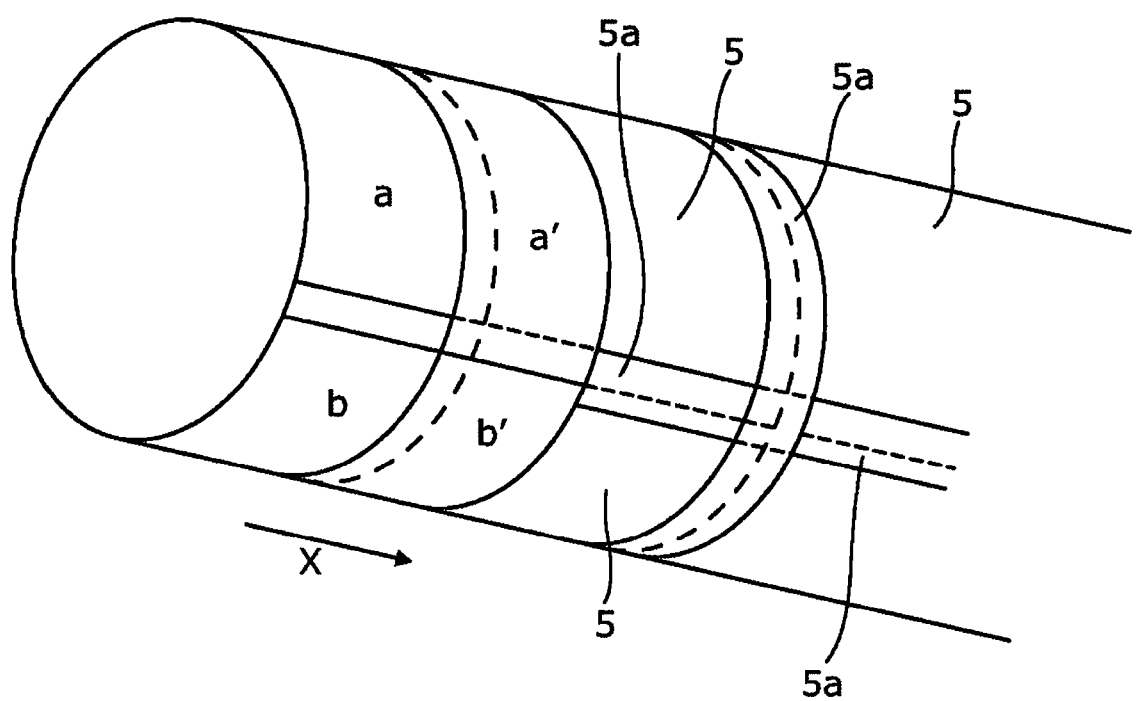
FIG. 4 is a schematic illustration of a tank partially lined according to the invention.

FIG. 4 illustrates a part of the method of installation of the invention. The different layers of sheet material of the double skin system of the invention are laid up on the wall of a tank that is oriented horizontally with sheets first being laid in the upper region of the tank between four and eight on a clock face, as indicated by letter a, a', followed by sheets being laid in the lower region of the tank between eight and four, as indicated by the letter 'b, 'b'.

Figure 5:
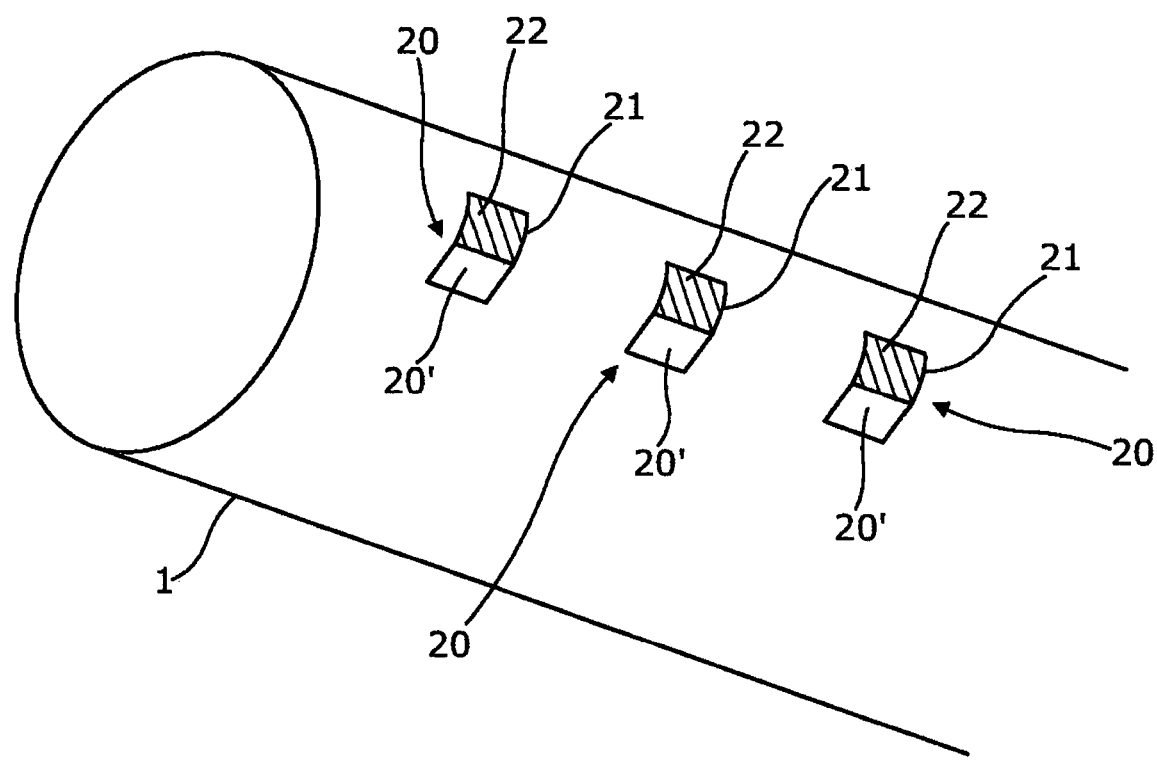
FIG. 5 illustrates an anchored fluid impervious wall skin according to an alternative embodiment of the invention.

Referring now to FIG. 5, there is shown a means of creating anchors 20 for anchoring the multi-layered skin to the tank wall 1. The anchors 20 are created after all of the layers of sheet material have been applied to the wall 1. A number of flaps 20' are cut in the built up layers 2-5 by cutting through the said layers to reveal the solvent free coating applied to the face of the wall 1. The coating revealed by pulling back the flap 20' is abraded, for example by sanding. A suitable adhesive 22, preferably an epoxy adhesive (which could be an epoxy filler or the solvent free epoxy resin coating used as an adhesive where the epoxy resin is not allowed to cure before the flap is pressed down), is applied to the abraded coating so as to cover the whole area 21 revealed by the flap (the flap may be 50 mm×50 mm). The flap is then pressed down on to the epoxy adhesive. When the epoxy adhesive has cured (a curing time of 30 minutes is typically allowed for) the final coat of solvent free resin is applied to the surface of the woven fibreglass cloth 5 and tape 5a following the process described above.

Figure 6:
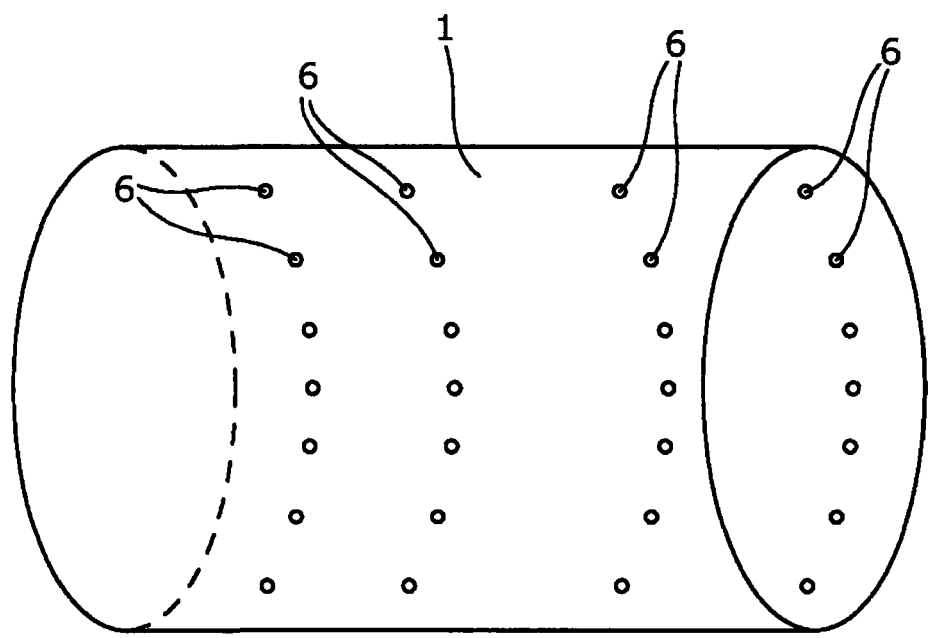
FIG. 6 illustrates an anchored fluid impervious wall skin according to another alternative embodiment of the invention.

FIG. 6 is illustrates an alternative means of creating anchors 16 for anchoring the multi-layer skin to the tank wall 1.

FIGS. 7 to 10 illustrate the anchors 16 in greater detail. Each anchor 6 includes a pin 9 extending from a base 7. The side of the base 7 proximate the wall 1 is attached thereto by adhesive. The adhesive may be applied directly to the base 7, or may be carried on a substrate. For example, a paper type material may be impregnated with adhesive or coated on both sides with adhesive. By virtue thereof the base sticks to the substrate and the substrate sticks to the wall 1. Note, the base 7 may be attached to the solvent free epoxy coating 2 rather than directly to the wall 1.

The layers 3, 4 and 5 are applied over the anchor 6, with the free end of pin 9 being sufficiently sharp to pierce the material of each layer 3-5 (note if the anchor happens to be aligned with tape 5a, then that also will be pierced).

In FIG. 7 the clasp 10 is shown as it is presented up to the free end of the pin 9. In FIG. 8, the clasp 10 has been pushed onto and along the pin 9 so that the clasp 10 presses against the surface of the woven fibreglass material 5, 5a.

Figure 10:
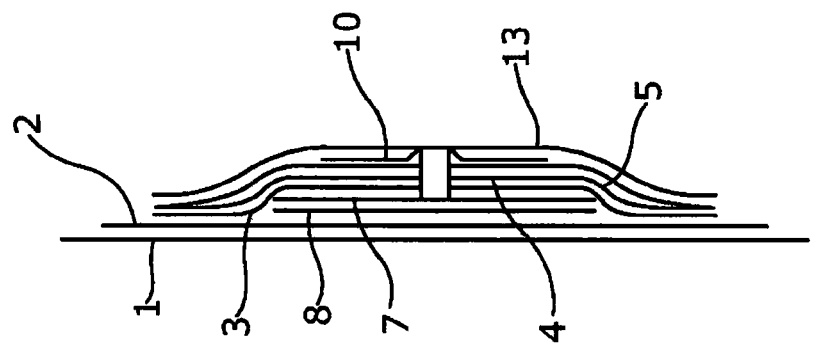
FIG. 10 is a cross-sectional elevation of the anchored wall skin illustrated in FIGS. 6 to 9 in a final stage of construction.
Figure 9:
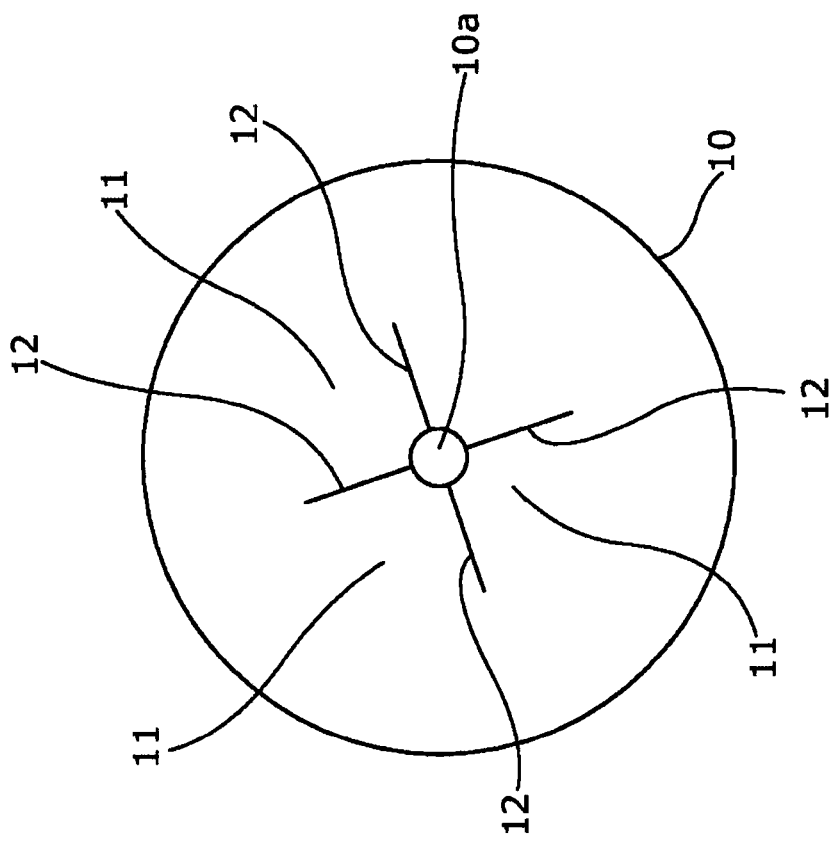
FIG. 9 is a plan view of a component of the anchored wall skin illustrated in FIGS. 6 to 8.

Referring now in particular to FIGS. 9 and 10, the clasp 10 includes an opening 10a which is slightly smaller in diameter than the pin 9. Slots 12 are cut in the clasp 10 so that when the clasp 10 is pressed on to the pin 9 the opening 10a can become larger, thereby allowing the clasp 10 to be pressed on to the surface of the layer 5. Any force acting in the opposite direction that would tend to push the clasp 10 off the pin 9 causes the opening 10a to close on to the pin 9, friction therebetween resisting movement of the clasp along the pin away from the base 7.

With the clasp in place, as shown in FIG. 8, the pin 9 is cut off adjacent the clasp 10 is cut off as shown in FIG. 10. The pin 9 is cut so that its free end is in a plane as close as possible to the plane of the free surface of the clasp 10, thereby avoiding unwanted protrusions. The final solvent free epoxy coating 6 is applied to the surface of the woven fibreglass sheet 5, tape 5a and the clasp 10 and the end of pin 9.

Typically, where the structure is oriented horizontally or substantially horizontally anchors are only desirable where the structure has a diameter exceeding 3 metres. Further, where anchors are used, they are placed from the horizontal centre-line upwards. On vertically oriented structures, such as an above ground tank, anchors can be installed to hold the double skin materials to the tank vertical wall and are typically desirable from a point 1 metre from tank floor and above.

Figure 11A:
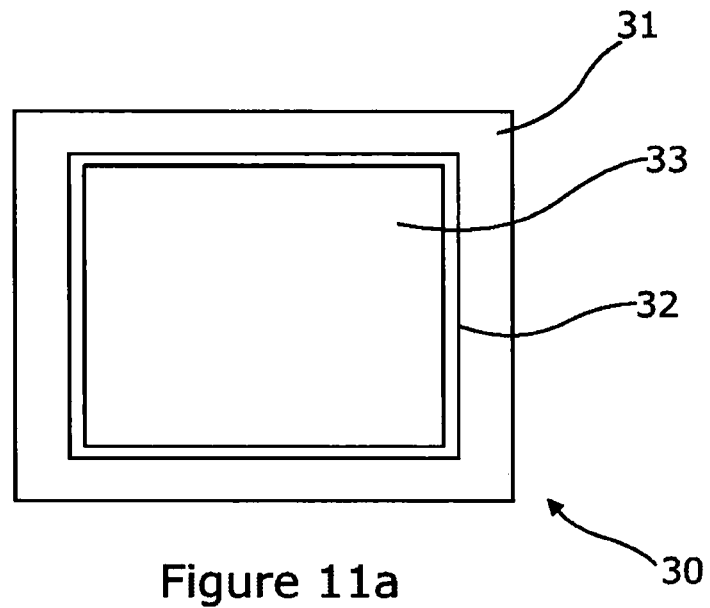
FIG. 11a is a plan view of an inspection assembly comprising a plate for attachment to a tank wall and an inspection port box connected thereto.

Above-ground structures (tanks in particular) are susceptible to external corrosion, especially in the bottom wall thereof, which is often inaccessible. FIG. 11a illustrates an inspection assembly 30 comprising a plate 31 for attachment to a tank wall and an inspection port box 32. The plate 31 includes a hole 31a. The inspection port box 32 also includes a hole 32a which aligns with the hole 31a when the inspection port box 32 is mounted on the plate 31. The inspection port box 32 is welded to the plate 31. The inspection port box 32 is provided with a lid 33 that is removable from the box 32. A seal, not shown, is provided between the lid 33 and the box 32.

Figure 11B:
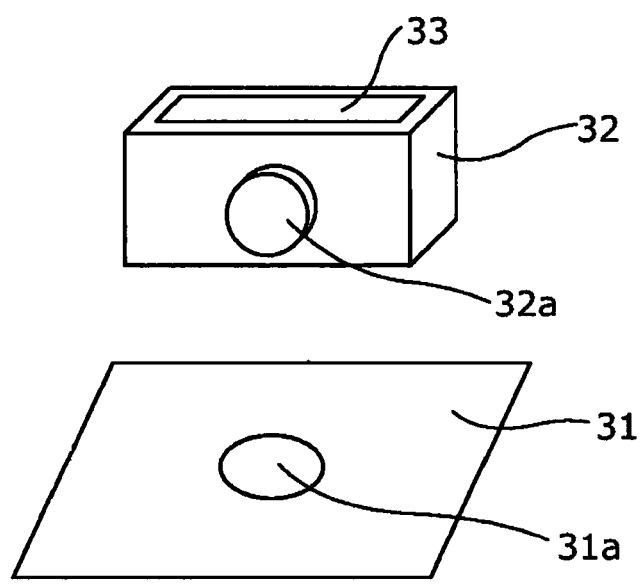

The inspection assembly 30 illustrated in FIGS. 11*a* and 11*b* is relatively small, the port plate being approximately 115 mm×115 mm, with the inspection port box 32 being approximately 76 mm×76 mm. The holes 31*a*, 32*a* in the example are approximately 50 mm in diameter. The sizes of the components of the inspection assembly are given by way of example only.

Figure 12:
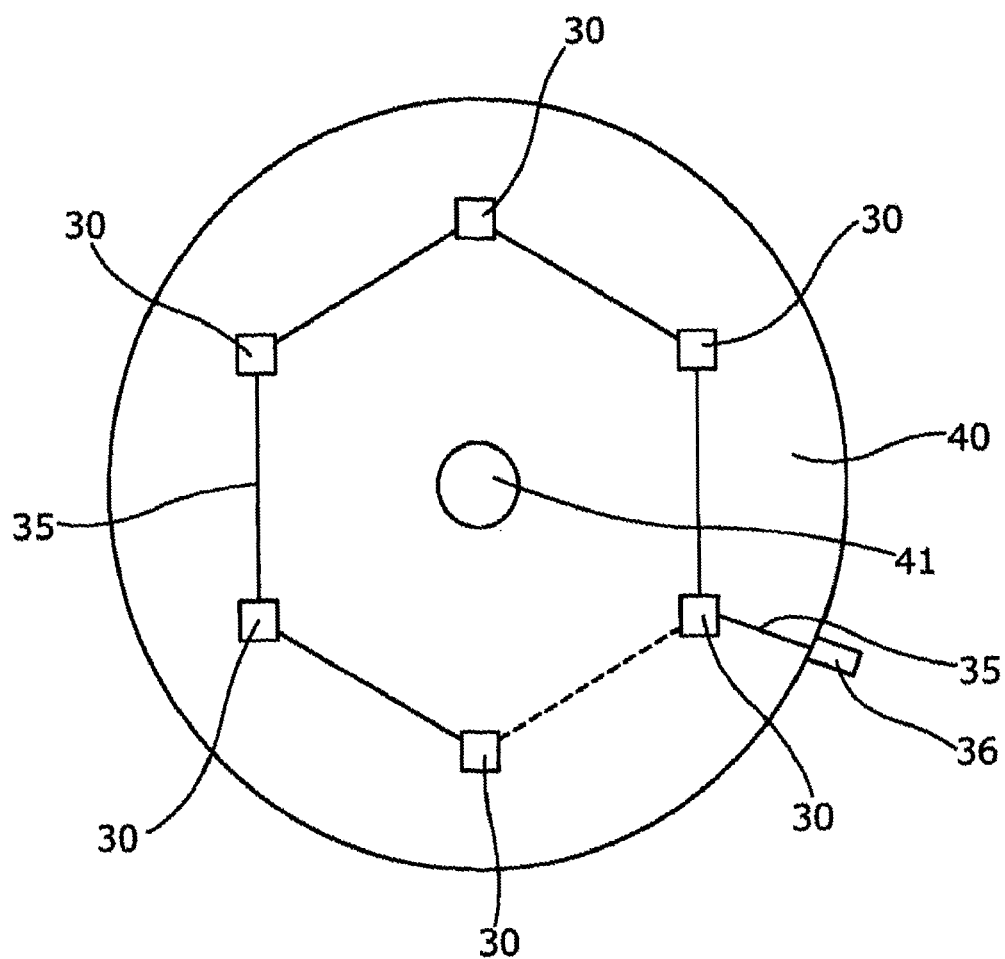
FIG. 12 illustrates a tank bottom wall provided with a plurality of inspection assemblies of the type illustrated in FIGS. 11a and 11b with provision for remote monitoring.

FIG. 12 illustrates the inside surface of the bottom wall 40 of an above-ground tank, the bottom wall 40 being provided with a sump 41. In the illustrated example, six inspection assemblies 30 are attached to the bottom wall 40 at spaced apart locations. The fluid impervious skin described above in relation to FIGS. 1 to 10 is brought up to the edge of the plate 31 or to the side wall of the inspection box 32. Those components of the inspection assembly 30 that are not covered by the fluid impervious skin are coated with a fluid impervious resin.

Figure 13:
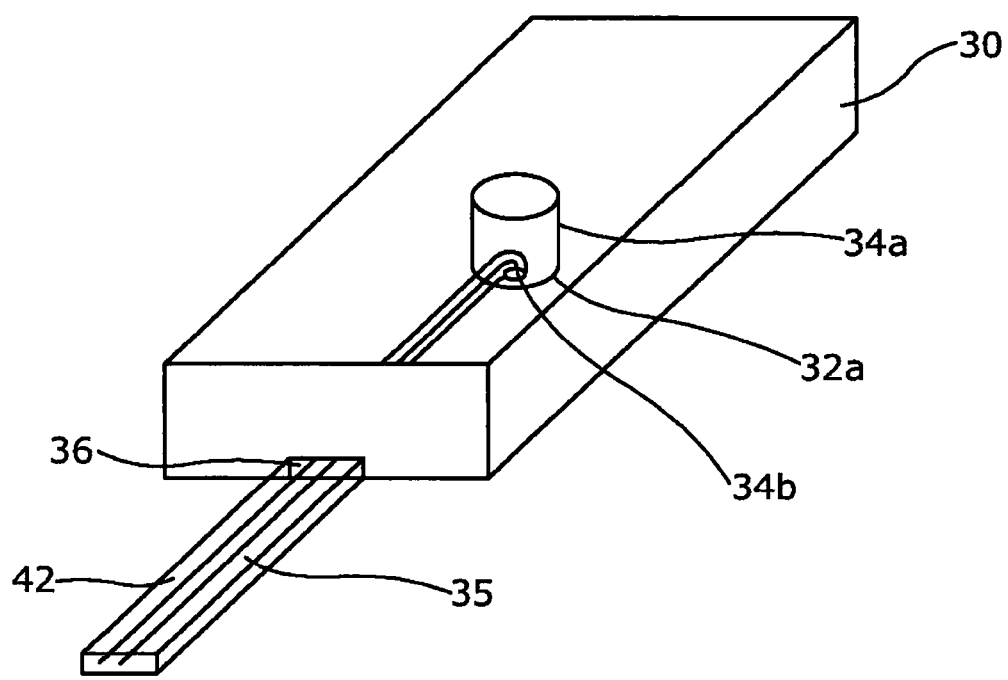
FIG. 13 is a schematic representation of the inspection box illustrated in FIGS. 11a and 11b provided with instrumentation.

Referring now to FIGS. 12 and 13, the inspection boxes 32 are provided with sensor ports 34*a* each equipped with a sensor 34*b* for monitoring the condition of the bottom wall 40. The sensor ports 34*a* each comprise a block of metal such as mild steel in which the sensor 34*b* is mounted. The sensors 34*b* may be ultrasonic sensors. Signals from the sensors may be conveyed to an external data receiving system by wires 35 or by means of wireless communication. In the wired arrangement illustrated in FIGS. 12 and 13 the inspection boxes 32 are provided with ports 36 through which the wires 35 pass. The ports 36 are sealed agains ingress of fluid when the wires have been passed through the ports. It is preferred that the wires 35 are encapsulated and therefore separated from the contents of the tank. In the illustrated example, trunking 42 is provided. This trunking may sit on top of the fluid impervious wall skin covering the bottom wall 40. The wires 35 exit the tank via a pipe penetration apparatus which allows the wires 35 to be accessed whilst preventing egress of fluid from the tank. Alternatively, the wires 35 may be arranged so that they exit the tank via the uppermost part thereof.

The inspection boxes 32 illustrated in FIGS. 11*a* to 13 provided for manual inspection of the bottom wall 40. Inspection is carried out by draining the content of a tank, for example via sump 41, entering the tank and removing the lid 33. The bottom wall 40 may be inspected visually through the holes 31*a*, 32*a* or by using non destructive testing equipment that is brought to the tank.

By providing for both manual and remote inspection it is possible that manual inspection cycles may be lengthened, whilst providing for corrosion to be detected earlier than high occur with manual inspection only.

Figure 14:
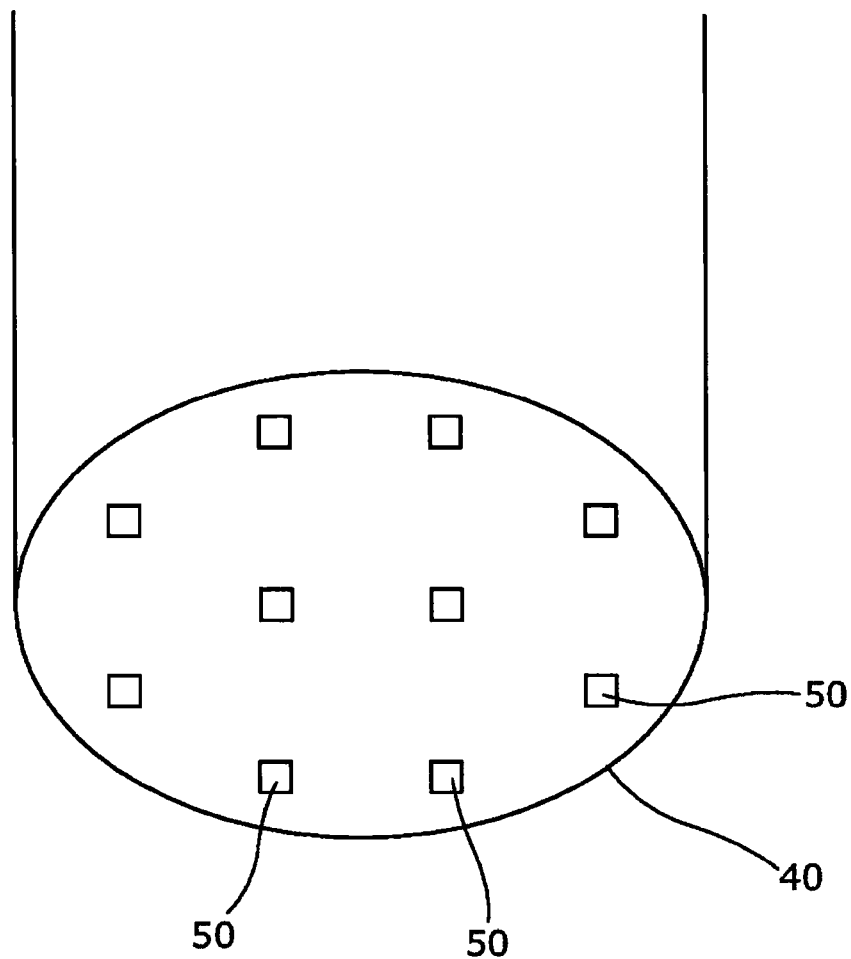
FIG. 14 illustrates a tank bottom wall provided with an alternative type of monitoring arrangement.

FIG. 14 illustrates a bottom wall 40 of an above-ground tank that is instrumented with sensors 50, typically ultrasound sensors, which are encapsulated within the flexible wall skin illustrated in and described with reference to FIGS. 1 to 10. In this arrangement, manual inspection of the bottom wall 40 is not possible. The ultrasound sensors 50 are equipped are wireless enabled so that data can be transmitted to an external data receiver. Alternatively, the sensor 50 could be connected by wires to an external data receiver.

Figure 15:
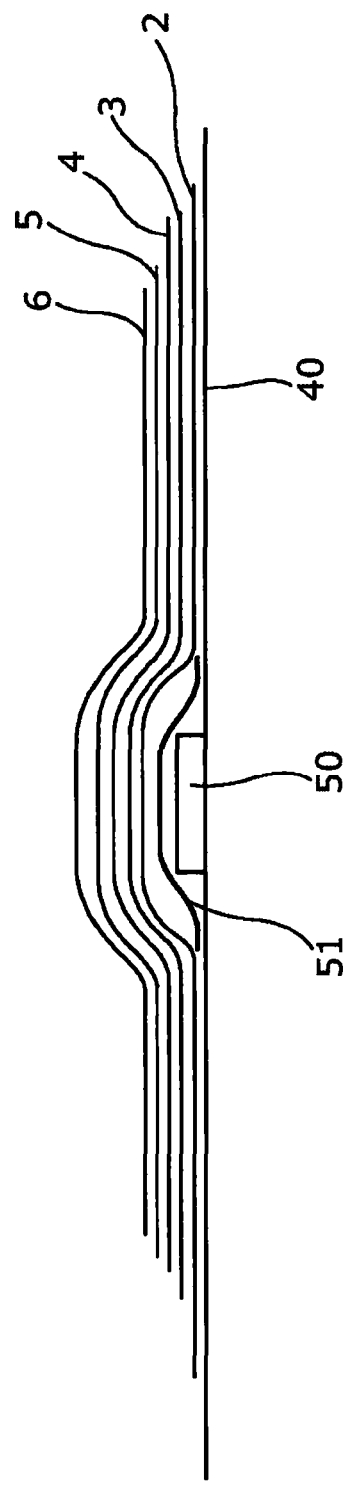
FIG. 15 is a schematic cross-sectional view of the mounting arrangement illustrated in FIG. 14.

FIG. 15 illustrates one of the sensors 50 situated between the bottom wall 40 and the layers 2 to 6 of the fluid impervious skin as described generally with reference to FIG. 1 for example. The sensor 50 is attached by means of a suitable adhesive to the surface of the structural wall after blasting thereof to provide a clean surface. A protective cap 51 is located over the sensor 50. The cap 51 is also attached to the surface of the structural wall 40 by adhesive. The function of the cap 51 is to protect the sensor 50 from inadvertent damage, for example if the sensor 50 were to be walked on. The cap may be formed from pressed steel or a plastic.

The invention has been described in relation to a tank. However, other types of structure may benefit from the invention. For example, wind turbine towers, oil rig legs, large diameter pipes, etc. In relation to tanks, it is not only fuel tanks that may benefit from a wall skin as described herein. Many liquids have corrosive properties and hence preventing contact between such liquids and the structural wall may be useful. Also, liquids may not be corrosive to a structure, but they may be harmful to the environment if they escape. Hence, providing an additional barrier in combination with a leak monitoring system is beneficial.

The invention claimed is:

1. A fluid impervious wall skin providing an interstitial space, the wall skin formed from a composite material, the composite material comprising a plurality of layers including:
   i. a first layer of flexible material having adhesive on at least one surface thereof for attachment to a structural wall;
   ii. a layer comprising a spacer; and
   iii. a second layer of flexible material; wherein layers of the composite material are attached a structural wall and one to the other by adhesive between adjacent layers, and wherein the spacer provides the interstitial space between the said first and second layers of flexible material within the said composite material, characterised by: the second flexible layer comprising overlapping sheets of a woven fibreglass fabric of a first weight and a woven fibreglass fabric tape of a second weight, the first weight heavier than the second weight, wherein the each overlapping sheet presents a free edge comprising ends of fibers, and the tape is positioned over the free edge and the overlapped sheet of woven fibreglass fabric of the first weight, and a solvent free epoxy coating applied to the surface of the second flexible layer that is distal from the structural wall, which coating cures to form a hard fluid impervious layer.

2. A fluid impervious wall skin according to claim 1, further comprising a third layer of flexible material, wherein the third layer is itself fluid impervious and wherein the third layer is situated between the spacer and the second layer of flexible material.

3. A fluid impervious wall skin according to claim 1, wherein the first layer of flexible material is coated with adhesive on both sides thereof.

4. A fluid impervious wall skin according to claim 1, wherein the first layer of flexible material is selected from the group consisting: paper, paper coated with adhesive, paper impregnated with adhesive, plastics film, and plastics film coated with adhesive.

5. A fluid impervious wall skin according to claim 2, wherein the third layer is selected from the group consisting: a metallic foil, a vinyl film and a pvc film.

6. A fluid impervious wall skin according to claim 1, wherein the second layer is coated with adhesive on one side thereof.

7. A fluid impervious wall skin according to claim 2, wherein the third layer is coated with adhesive on one side thereof.

8. A fluid impervious wall skin according to claim 1, including a peel off layer for each adhesive coated surface.

9. A fluid impervious wall skin according to claim 1, wherein the spacer is selected from the group consisting: a permeable membrane; a permeable membrane that is a thermoplastic; a permeable membrane that is a non-woven grid; and a permeable membrane that is a thermoplastic non-woven grid.

10. A fluid impervious wall skin according to claim 1, wherein the wall skin includes a coating of solvent free epoxy coating applied to the inner surface of the structural wall, the first layer attached to the cured structural wall coating.

11. A fluid impervious wall skin according to claim 1, wherein the woven fibreglass fabric of a first weight weighs a selected one of: between 150 g/m2 and 250 g/m2; between 175 g/m2 and 225 g/m2; 190 g/m2 and 210 g/m2; and 200 g/m2 and a woven fibreglass fabric tape of a second weight weighs a selected one of: between 50 and 150 g/m2; between 75 and 125 g/m2; between 90 and 110 g/m2; and 106 g/m2.

12. A fluid impervious wall skin according to claim 1, wherein the solvent free epoxy coating has a nominal thickness of a selected one of: at least 1000 micron and at least 2000 micron.

13. A fluid impervious wall skin according to claim 1, wherein in an area occupied by the woven fibreglass fabric tape the solvent free epoxy coating has a nominal thickness that is double the nominal thickness of the solvent free epoxy coating between adjacent tape covered overlapped edges.

14. A fluid impervious wall skin according to claim 1, further comprising a selected one of: a plurality of anchors, each anchor spaced apart relative to other anchors of the plurality of anchors; a plurality of anchors, each anchor spaced apart relative to other anchors of the plurality of anchors and wherein the plurality of anchors are situated in an upper region of the structure; a plurality of anchors, each anchor spaced apart relative to other anchors of the plurality of anchors and wherein each anchor comprises an additional adhesive between the first layer and the structural wall; and a plurality of anchors, each anchor spaced apart relative to other anchors of the plurality of anchors, wherein the plurality of anchors are situated in an upper region of the structure and wherein each anchor comprises an additional adhesive between the first layer and the structural wall.

15. A fluid impervious wall skin according to claim 14, wherein each anchor comprises a pin and clasp, the pin projecting through the layers of flexible material, and the clasp mounted on the pin and pressing against the surface of the second layer of flexible material distal from the structural wall, and wherein the clasp and the end of the pin are encapsulated by the solvent free epoxy coating.

16. A fluid impervious wall skin according to claim 10, wherein the structural wall coating has a nominal thickness of a selected one of: at least 500 micron and at least 1270 micron.

17. A fluid impervious wall skin according to claim 1, wherein the hard fluid impervious layer has a Shore D hardness reading in the range of 85.5 to 87.5.

18. A fluid impervious wall skin according to claim 1, further comprising at least one housing attached to the structural wall and extending to the same side thereof as the wall skin, the housing having a removable and closure member that is fluid tight when closed, wherein at least the closure member of each at least one housing is not covered by the fluid impervious wall skin, the housing providing access to a part of the structural wall.

19. A fluid impervious wall skin according to claim 18, wherein the at least one housing includes a selected one of: a plate for attachment to the structural wall and a chamber that is attached to the plate, the closure member located in an opening in the chamber; and a plate for attachment to the structural wall and a chamber that is attached to the plate, the closure member located in an opening in the chamber and wherein the plate has an opening therein through which access to the structural wall may be gained, and wherein the chamber has a corresponding opening, the two openings being aligned when the chamber is mounted on the plate.

20. A fluid impervious wall skin according to claim 1, further comprising monitoring means configured for monitoring the condition of the structural wall.

21. A fluid impervious wall skin according to claim 20, wherein the monitoring means comprises a selected one of: at least one sensor; at least one sensor wherein the at least one sensor is connected to an external data receiving by one of a wired and wireless connection; at least one sensor, wherein the at least one sensor is situated between the structural wall and the first layer of flexible material of the wall skin; at least one sensor, wherein the at least one sensor is connected to an external data receiving by one of a wired and wireless connection and wherein the at least one sensor is situated between the structural wall and the first layer of flexible material of the wall skin.

22. A fluid impervious wall skin according to claim 18, further comprising monitoring means configured for monitoring the condition of the structural wall, and wherein the monitoring means is mounted in a selected one of: the housing and a protective member.

\* \* \* \* \*